(12) United States Patent
Tanoury et al.

(10) Patent No.: US 8,383,858 B2
(45) Date of Patent: Feb. 26, 2013

(54) PROCESSES AND INTERMEDIATES FOR PREPARING STERIC COMPOUNDS

(75) Inventors: Gerald J. Tanoury, Hudson, MI (US); Minzhang Chen, Acton, MA (US); Young Chun Jung, Lexington, MA (US); Raymond E. Forslund, Natick, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 265 days.

(21) Appl. No.: 12/806,014

(22) Filed: Aug. 4, 2010

(65) Prior Publication Data
US 2010/0298568 A1 Nov. 25, 2010

Related U.S. Application Data

(63) Continuation of application No. 11/724,002, filed on Mar. 14, 2007, now abandoned.

(60) Provisional application No. 60/782,976, filed on Mar. 16, 2006, provisional application No. 60/844,771, filed on Sep. 15, 2006.

(51) Int. Cl.
*C07J 9/00* (2006.01)
*C07C 233/06* (2006.01)

(52) U.S. Cl. .......................... 564/193; 552/549

(58) Field of Classification Search .................. 564/193; 552/549
See application file for complete search history.

(56) References Cited

U.S. PATENT DOCUMENTS

| | | | |
|---|---|---|---|
| 6,025,516 A | 2/2000 | Ramaswamy et al. | |
| 6,348,608 B1 | 2/2002 | Shi | |
| 6,833,442 B2 | 12/2004 | Shibasaki et al. | |
| 7,034,178 B2 | 4/2006 | Faber et al. | |
| 7,612,337 B2 | 11/2009 | Suzuki et al. | |
| 2003/0153788 A1 | 8/2003 | Kobayashi et al. | |
| 2005/0197299 A1 | 9/2005 | Babine et al. | |

FOREIGN PATENT DOCUMENTS

| | | |
|---|---|---|
| JP | 2004155704 | 6/2004 |
| WO | WO0202546 | 1/2002 |
| WO | WO02/18369 | 3/2002 |
| WO | WO03/003804 | 1/2003 |
| WO | WO 2005/087731 | 9/2005 |
| WO | WO2006008170 | 1/2006 |

OTHER PUBLICATIONS

Behrens, Carl H., et al., "Selective Transformations of 2,3-Epoxy Alcohols . . . ", J. Org. Chem., 50, pp. 5696-5704 (1985).
Cacciola, Joseph, et al., "The Synthesis of Lysine a-Ketoamide Thrombin Inhibitors . . . ", Tetrahedron Letters, vol. 38, No. 33 pp. 5741-5744 (1977).
Kakei, Hiroyuki, et al., "Catalytic Asymmetric Epoxidation . . . ", J. Am. Chem. Soc., 127, pp. 8962-8963 (2005).
Kamandi, E., et al., "Die Synthese van b-Phenyl-isoserinen . . . ", Archiv der Pharmazie (Weinheim Germany) 307(11), 871-8 Coden: ARPMAS: ISSN:0365-6233, XP002442084 (1974).
Kino, Rie, et al., "remarkable effect of tris(4-fluorophenyl)phospine oxide on the stabilization . . . ", Org. Biomol. Chem., 2, pp. 1822-1824 (2004).
Marigo, Mauro, et al., "Asymmetric Organocatalytic Epoxidation of . . . ", J. Am. Chem. Soc., 127(19) pp. 6964-6965 (2005).
Taber, Douglass F., "Asymmetric Nucleophilic Epoxidation", Org. Chem. Highlights, (2004) http://www.organic-chemistry.org/highlights/2004/22November.shtm.
Wang, Zhi-Xian, et al., "Asymmetric Epoxidation of trans-b-Methylstyrene . . . ", Organic Syntheses, vol. 80, p. 9 (2003).
International Search Report, dated Jul. 23, 2007 for PCT/US2007/006320.
Eliel, E.L., et. al., Stereochemistry of Organic Compounds. New York: Wiley-Interscience, 1994, pp. 322-344.
PCT/US2007/006320—International Search Report (Jul. 23, 2007).
Chai Ling Fan, et. al., Journal of Organic Chemistry (2003) 68, pp. 9816-9818, p. 9817, Table 1.

*Primary Examiner* — Bernard Dentz
(74) *Attorney, Agent, or Firm* — Honigman Miller Schwartz and Cohn LLP; Heidi M. Berven; Jonathan P. O'Brien

(57) ABSTRACT

This invention relates to processes and intermediates for the preparation of an alpha-amino beta-hydroxy acid of Formula 1

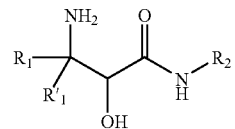

wherein the variables $R_1$, $R'_1$ and $R_2$ are defined herein and the compound of Formula 1 has an enantiomeric excess (ee) of 55% or greater.

1 Claim, No Drawings

PROCESSES AND INTERMEDIATES FOR PREPARING STERIC COMPOUNDS

CROSS-REFERENCE

This application is a continuation of U.S. Ser. No. 11/724,002, filed Mar. 14, 2007 and claims the benefits of U.S. Provisional Application Serial No. 60/782,976, filed Mar. 16, 2006, and U.S. Provisional Application Serial No. 60/844,771, filed Sep. 15, 2006, the entire contents of which are incorporated herein by reference.

FIELD OF THE INVENTION

This invention relates to processes and intermediates for the preparation of protease inhibitors, in particular, serine protease inhibitors.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone. [M. J. Alter et al., "The Epidemiology of Viral Hepatitis in the United States, Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV, only about 20% of infected individuals develop acute clinical hepatitis while others appear to resolve the infection spontaneously. In almost 70% of instances, however, the virus establishes a chronic infection that may persist for decades. [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. Prolonged chronic infection can result in recurrent and progressively worsening liver inflammation, which often leads to more severe disease states such as cirrhosis and hepatocellular carcinoma. [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

Compounds described as protease inhibitors, and in particular serine protease inhibitors, useful in the treatment of HCV infections are disclosed in WO 02/18369. Also disclosed therein are processes and intermediates for the preparation of these compounds. There remains however, a need for economical processes for the preparation of these compounds.

SUMMARY OF THE INVENTION

This invention relates to processes and intermediates for the preparation of an alpha-amino beta-hydroxy acid of Formula 1

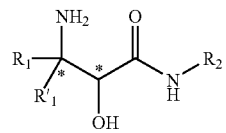

wherein the variables $R_1$, $R'_1$ and $R_2$ are defined herein and the compound of Formula 1 has an enantiomeric excess (ee) of 55% or greater.

The process comprises the steps of oxidizing an unsaturated amide or ester to form the corresponding epoxide, forming an alpha-hydroxy, beta-amino acid with an appropriate aminating reagent and resolving the amino-alcohol amide.

The processes and intermediates are particularly directed to the preparation of (2S,3S)-3-amino-N-cyclopropyl-2-hydroxyhexanamide.

These processes and intermediates are useful for the preparation of a protease inhibitor of Formula 2, wherein the variables $R_3$ and $R_4$ are defined herein.

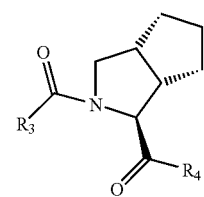

In one aspect, the invention features processes and intermediates used in the preparation of the serine protease inhibitor of Formula 3.

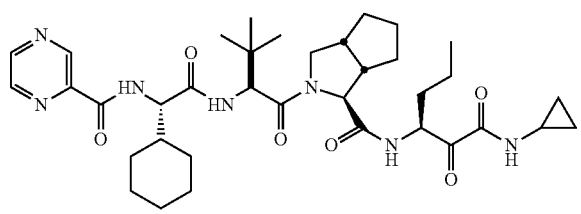

DETAILED DESCRIPTION OF THE INVENTION

I. Definitions

As used herein, the term "enantimoeric excess (ee) of 55% or greater" means that one enantiomer is present 55% or more than the other in a chemical substance. The enantiomer can be a result of either the carbon center to which the amino group is bonded (shown with an asterisk) in Formula 1

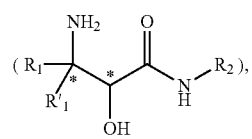

or the carbon center to which the hydroxyl group is bonded (also shown with an asterisk) in Formula 1, or both carbon centers. For instance, numbered away from the carbonyl group, the compound can be (2S,3S), (2S,3R), (2R,3R) or (2R,3S) in these two carbon centers.

As used herein, "organic bases" that may be used in a process of this invention include tertiary organic bases that include, but are not limited to trialkylamines, e.g. diethylisopropylamine, triethylamine, N-methylmorpholine and the like, and heteroaryl amines, e.g. pyridine, quinoline, and the like.

As used herein, the term "aliphatic" encompasses alkyl, alkenyl, and alkynyl.

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as cycloalkyl, heterocycloalkyl, aryl, heteroaryl, alkoxy (two alkoxy groups on the same atom or adjacent atoms may form a ring together with the atom(s) to which they are bound), aroyl, heteroaroyl, alkoxycarbonyl, alkylcarbonyloxy, acyl, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, carbamoyl.cycloalkyloxy, heterocycloalkyloxy, aryloxy, heteroaryloxy, aralkyloxy, heteroarylalkoxy, amino, nitro, carboxy, cyano, oxo, halo, hydroxy, sulfo, mercapto, alkylsulfanyl, alkylsulfinyl, alkylsulfonyl, aminocarbonyl, alkylcarbonylamino, cycloalkylcarbonylamino, cycloalkylalkylcarbonylamino, arylcarbonylamino, aralkylcarbonylamino, heterocycloalkyl-carbonylamino, heterocycloalkylalkylcarbonylamino, heteroarylcarbonylamino, or heteroaralkylcarbonylamino.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as cycloalkyl, heterocycloalkyl, aryl, heteroaryl, alkoxy (two alkoxy groups on the same atom or adjacent atoms may form a ring together with the atom(s) to which they are bound), aroyl, heteroaroyl, alkoxycarbonyl, alkylcarbonyloxy, acyl, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, carbamoyl.cycloalkyloxy, heterocycloalkyloxy, aryloxy, heteroaryloxy, aralkyloxy, heteroarylalkoxy, amino, nitro, carboxy, cyano, oxo, halo, hydroxy, sulfo, mercapto, alkylsulfanyl, alkylsulfinyl, aminocarbonyl, alkylcarbonylamino, cycloalkylcarbonylamino, cycloalkylalkylcarbonylamino, arylcarbonylamino, aralkylcarbonylamino, heterocycloalkyl-carbonylamino, heterocycloalkylalkylcarbonylamino, heteroarylcarbonylamino, or heteroaralkylcarbonylamino.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as cycloalkyl, heterocycloalkyl, aryl, heteroaryl, alkoxy (two alkoxy groups on the same atom or adjacent atoms may form a ring together with the atom(s) to which they are bound), aroyl, heteroaroyl, alkoxycarbonyl, alkylcarbonyloxy, acyl, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, carbamoyl, cycloalkyloxy, heterocycloalkyloxy, aryloxy, heteroaryloxy, aralkyloxy, heteroarylalkoxy, amino, nitro, carboxy, cyano, oxo, halo, hydroxy, sulfo, mercapto, alkylsulfanyl, alkylsulfinyl, alkylsulfonyl, aminocarbonyl, alkylcarbonylamino, cycloalkylcarbonylamino, cycloalkylalkylcarbonylamino, arylcarbonylamino, aralkylcarbonylamino, heterocycloalkyl-carbonylamino, heterocycloalkylalkylcarbonylamino, heteroarylcarbonylamino, or heteroaralkylcarbonylamino.

As used herein, an "amino" group refers to —NRXRY wherein each of RX and RY is independently hydrogen, alkyl, cycloalkyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —NRX—. RX has the same meaning as defined above.

As used herein, an "aryl" group used alone or as part of a larger moiety as in "aralkyl", "aralkoxy", or "aryloxyalkyl" refers to phenyl, naphthyl, or a benzofused group having 2 to 3 rings. For example, a benzofused group includes phenyl fused with one or two C4-8 carbocyclic moieties, e.g., 1,2,3,4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl), sulfinyl (such as alkylsulfinyl), sulfanyl (such as alkylsulfanyl), sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" are defined herein. An example of an aralkyl group is benzyl. An "heteroaralkyl" group refers to an alkyl group that is substituted with a heteroaryl. Both "alkyl" and "heteroaryl" are defined herein. As used herein, a "cycicoaliphatic" group encompasses a "cycloalkyl" group and a "cycloalkenyl" group.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.3.2.]decyl, and adamantyl. A "cycloalkenyl" group, as used herein, refers to a non-aromatic carbocyclic ring of 3-10 (e.g., 4-8) carbon atoms having one or more double bond. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]octenyl, and bicyclo[3.3.1]nonenyl. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl.

As used herein, the term heterocycloaliphatic encompasses a heterocycloalkyl group and a heterocycloalkenyl group.

As used herein, a "heterocycloalkyl" group refers to a 3- to 10-membered mono- or bicylic (fused or bridged) (e.g., 5- to 10-membered mono- or bicyclic) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiopheneyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.03,7] nonyl. A monocyclic heterocycloalkyl group may be fused with a phenyl moiety such as tetrahydroisoquinoline. A "heterocycloalkenyl" group, as used herein, refers to a mono- or bicylic (e.g., 5- to 10-membered mono- or bicyclic) nonaromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl (such as a benzimidazolidinyl), (heterocycloalkyl)alkyl, aryl, heteroaryl, alkoxy (two alkoxy groups on the same atom or adjacent atoms may form a ring together with the atom(s) to which they are bound), cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl.

A "heteroaryl" group, as used herein, refers to a monocylic, bicyclic, or tricyclic ring structure having 4 to 15 ring atoms wherein one or more of the ring atoms is a heteroatom, e.g., N, O, or S and wherein one or more rings of the bicyclic or tricyclic ring structure is aromatic. A heteroaryl group includes a benzofused ring system having 2 to 3 rings. For example, a benzofused group includes phenyl fused with one or two C4-8 heterocyclic moieties, e.g., indolinyl and tertahydroquinolinyl. Some examples of heteroaryl are azetidinyl, pyridyl, furyl, pyrrolyl, thienyl, thiazolyl, oxazolyl, imidazolyl, indolyl, tetrazolyl, benzofuryl, isoquinolinyl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or alkyl-C(=O)— where "alkyl" has been defined previously. Acetyl and pivaloyl are examples of acyl groups.

As used herein, a "carbamoyl" group refers to a group having the structure —O—CO—NrxRy or —NRx-CO—O-Rz wherein Rx and Ry have been defined above and Rz can be alkyl, aryl, aralkyl, heterocycloalkyl, heteroaryl, or heteroaralkyl.

As used herein, a "carboxy" and a "sulfo" group refer to —COOH or —COOR$_X$ and —SO$_3$H or —SO$_3$R$_X$, respectively.

As used herein, an "alkoxy" group refers to an alkyl-O— group where "alkyl" has been defined previously.

As used herein, a "sulfoxy" group refers to —O—SO—R$_X$ or —SO—O—R$_X$, where R$_X$ has been defined above.

As used herein, a "sulfonyl" group refers to —S(O)$_2$—R$_X$, wherein R$_X$ has been defined above.

As used herein a "sulfinyl" group refers to —S(O)—R$_X$, wherein R$_X$ has been defined above.

As used herein a "sulfanyl" group refers to —S—R$_X$, wherein R$_X$ has been defined above.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —CF$_3$.

As used herein, a "sulfamoyl" group refers to the structure —S(O)$_2$—NR$_x$R$_y$, or —NR$_x$—S(O)$_2$—Rz wherein Rx, Ry, and Rz have been defined above.

As used herein, a "sulfamide" group refers to the structure —NR$_X$—S(O)$_2$—NR$_Y$R$_Z$ wherein R$_X$, R$_Y$, and R$_Z$ have been defined above.

As used herein, a "carbonylamino" group used alone or in connection with another group refers to an amido group such as —C(O)—NR$_X$—, —NR$_X$—C(O)—, and —C(O)—N(R$_X$)$_2$. For instance an alkylcarbonylamino includes alkyl-C(O)—NR$_X$— and alkyl-NR$_X$—C(O)—.

As used herein, a "urea" group refers to the structure —NR$_X$—CO—NR$_Y$R$_Z$ and a "thiourea" group refers to the structure —NR$_X$—CS—NR$_Y$R$_Z$. R$_X$, R$_Y$, and R$_Z$ have been defined above.

The phrase "optionally substituted" is used interchangeably with the phrase "substituted or unsubstituted." As described herein, compounds of the invention may optionally be substituted with one or more substituents, such as are illustrated generally above, or as exemplified by particular classes, subclasses, and species of the invention. As described herein, the variables encompass specific groups, such as alkyl and aryl. Unless otherwise noted, each of the specific groups for the variables may be optionally substituted with one or more substituents described herein. Each substituent of a specific group is further optionally substituted with one to three of halo, cyano, alkoxy, hydroxyl, nitro, haloalkyl, and alkyl. For instance, an alkyl group may be substituted with alkylsulfanyl and the alkylsulfanyl may be optionally substituted with one to three of halo, cyano, alkoxy, hydroxyl, nitro, haloalkyl, and alkyl. As an additional example, the cycloalkyl portion of a (cycloalkyl)carbonylamino may be optionally substituted with one to three of halo, cyano, alkoxy, hydroxyl, nitro, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, the term "bicyclic fused ring system" or "bicyclic ring system" refers to two rings which share two atoms. Either ring may be saturated, partially unsaturated, or aromatic. Each ring also may contain 1 to 3 heteroatoms.

As used herein, the term "tricyclic fused ring system" or "tricyclic ring system" refers to a bicyclic ring system in which a third ring is fused to the bicyclic ring system such that the third ring shares at least two atoms with the bicyclic ring system. In some embodiments, all three rings share at least one common atom. Any of the rings in the tricyclic ring system may be saturated, partially unsaturated, or aromatic. Each of the rings may include 1 to 3 heteroatoms.

In some embodiments, aliphatic groups, alkyl groups, aryl groups, heterocyclic groups, carbocyclic groups, and bicyclic or tricyclic ring systems contain one or more substituents. The substituents are selected from those that will be stable under the reaction conditions of the present process, as would be generally known to those skilled in the art. Examples of substituents include halogen, $-Q_1$, $-OQ_1$, $-OH$, protected OH (such as acyloxy), phenyl (Ph), substituted Ph, $-OPh$, substituted $-OPh$, $-NO_2$, $-CN$, $-NHQ_1$, $-N(Q_1)_2$, $-NHCOQ_1$, $-NHCONHQ_1$, $-NQ_1CONHQ_1$, $-NHCON(Q_1)_2$, $-NQ_1CON(Q_1)_2$, $-NQ_1COQ_1$, $-NHCO_2Q_1$, $-NQ_1CO_2Q_1$, $-CO_2Q_1$, $-COQ_1$, $-CONHQ_1$, $-CON(Q_1)_2$, $-S(O)_2Q_1$, $-SONH_2$, $-S(O)Q_1$, $-SO_2NHQ_1$, $-SO_2N(Q_1)_2$, $-NHS(O)_2Q_1$, $-NQ_1S(O)_2Q_1$, $=O$, $=S$, $=NNHQ_1$, $=NN(Q_1)_2$, $=N-OQ_1$, $=NNHCOQ_1$, $=NNQ_1COQ_1$, $=NNHCO_2Q_1$, $=NNQ_1CO_2Q_1$, $=NNHSO_2Q_1$, $=NNQ_1SO_2Q_1$, or $=NQ_1$ where $Q_1$ is an optionally substituted aliphatic, aryl or aralkyl group.

As used herein, nitrogen atoms on a heterocyclic ring may be optionally substituted. Suitable substituents on the nitrogen atom include $Q_2$, $COQ_2$, $S(O)_2Q_2$, and $CO_2Q_2$, where $Q_2$ is an aliphatic group or a substituted aliphatic group.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The term "substantially pure" refers to the stereochemical purity of a compound that is greater than 90%. In some embodiments, the stereochemical purity of a compound is greater than 95%. And in still others, the stereochemical purity of a compound is 99% or greater.

The term "selective crystallization" means crystallization of a substantially pure isomer from a solvent containing a mixture of isomers.

The term "dynamic crystallization" means crystallization of a substantially pure isomer from a solvent containing a mixture of isomers under conditions which cause isomerization of the mixture of isomers to an isomer which selectively crystallizes. For example, in the case of resolving enantiomers, isomerization of the more soluble enantiomer to the less soluble isomer results in crystallization of the less soluble isomer as the equilibrium between the isomers is driven by crystallization toward the less soluble enantiomer. A specific example of dynamic crystallization may include the epimerization of an anomeric carbon in a solvent under conditions which selectively crystallizes one substantially pure enantiomer.

Unless otherwise stated, structures depicted herein are also meant to include compounds which differ only in the presence of one or more isotopically enriched atoms.

Various "protecting groups," "capping groups," or "amine capping groups" may be used in the methods of this invention. Examples of amine capping groups or protecting groups include, but are not limited to, $-Q^7$, $-C(O)Q^7$, $-C(O)OQ^7$, $-SOQ^7$, $-SO_2Q^7$, $-SO_3Q^7$, $-SO_2N(Q^7)_2$, $-C(O)C(O)Q^7$, $-C(O)C(O)OQ^7$, $-C(O)CH_2C(O)Q^7$, $-C(O)N(Q^7)_2$, $-(CH_2)_{0-2}NHC(O)Q^7$, $-C(=NH)N(Q^7)_2$, $-C(O)N(OQ^7)Q^7$, $-C(=NOQ^7)Q^7$, $-P(O)(Q^7)_2$, and $-P(O)(OQ^7)_2$; wherein $Q^7$ is hydrogen, an optionally substituted aliphatic group, an optionally substituted aryl group, or an optionally substituted heterocyclic group. Preferably, $Q^7$ is $C_{1-12}$ aliphatic, $C_{3-10}$ cycloaliphatic, $(C_{3-10}$ cycloaliphatic)-$C_{1-12}$ aliphatic, $C_{6-10}$ aryl, $(C_{6-10}$ aryl)-$(C_{1-12}$ aliphatic)-, $C_{3-10}$ heterocyclyl, $(C_{6-10}$ heterocyclyl)-$C_{1-12}$ aliphatic, $C_{5-10}$ heteroaryl, or $(C_{5-10}$ heteroaryl)-$(C_{1-12}$ aliphatic)-.

As used herein, the term "lewis acid" refers to moiety capable of sharing or accepting an electron pair. Examples of lewis acids include, but are not limited to, $BF_3$-etherates and metal halides, alkoxides, and mixed halide/alkoxides (e.g., Al(O-alkyl)$_2$Cl, Al(O-alkyl)Cl$_2$). The metals can be aluminum, titanium, zirconium, magnesium, copper, zinc, iron, tin, boron, ytterbium, lanthanum, and samarium.

EDCI is 1-(3-dimethylaminopropyl)-3-ethylcarbodiimide. HOBt is 1-hydroxybenzotriazole. HOSuc is N-hydroxysuccinimide. THF is tetrahydrofuran. TFA is trifluoroacetic acid. DCM is dichloromethane. DMAP is 4-dimethylaminopyridine. DIPEA is diisopropylethylamine. DMF is dimethylformamide. TFA is trifluoroacetic acid. CBZ is benzyloxycarbonyl. $^1$H NMR is proton nuclear magnetic resonance. TLC is thin layer chromatography. TEMPO is 2,2,6,6-Tetramethylpiperidinyloxy free radical.

II. Processes and Intermediates

Generally, this invention relates to processes for and intermediates used in the preparation of steric-specific compounds.

Specifically, the processes and intermediates described herein are useful for the preparation of an HCV protease inhibitor of Formula 2.

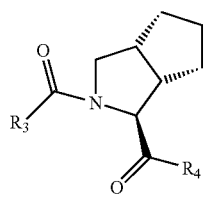

2 wherein
$R_3$ is RW— or a P4-L3-P3-L2-P2-;
$R_4$ is —NH—$CR_1R'_1$—CH(OH)C(O)—$NHR_2$;
Each W is independently a bond, —$NR_4$, —O— or —S—;
Each of P2, P3 and P4 is independently a bond, H, an optionally substituted aliphatic, an optionally substituted heteroaliphatic, an optionally substituted aryl, an optionally substituted heteroaryl, an optionally substituted alkoxy, an optionally substituted alkylsufanyl, an optionally substituted aralkoxy, an optionally substituted aralkylsulfanyl, an optionally substituted mono- or dialkylamino, an optionally substituted mono- or diarylamino or an optionally substituted mono- or diheteroarylamino, provided that
when L2 is absent and P3 is H, that L3 and P4 are absent;
when P2 is not a terminal group, that P2 is bound to the core structure of formula 3 and P2 is also bound to L2, if present, or P3, if L2 is absent;
when P3 is not a terminal group, that P3 is bound to L2, if present, or P2, if L2 is absent, and P3 is also bound to L3, if present, or P4, if L3 is absent;
Each L2 or L3 is independently a bond, —C(O)— or —$SO_2$—;
Each $R_1$ and $R'_1$, is independently H, an optionally substituted aliphatic, an optionally substituted aryl, an optionally substituted aralkyl, an optionally substituted heteroaliphatic or an optionally substituted heteroaralkyl, or each $R_1$ and $R'_1$, together with the atom to which they are attached may form a 3 to 7 membered optionally substituted cycloaliphatic ring.

In some embodiments $R_3$ is P2-, which is represented by the structure:

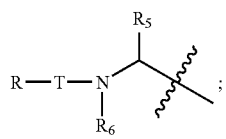

wherein
Each T is independently a bond, H, —C(O)—, —O—C(O)—, —NHC(O)—, —C(O)C(O)— or —$SO_2$—;
Each R is independently H, an optionally substituted aliphatic, an optionally substituted heteroaliphatic, an optionally substituted cycloaliphatic, an optionally substituted heterocyclic, an optionally substituted aralkyl, an optionally substituted heteroaralkyl, an optionally substituted aryl or an optionally substituted heteroaryl; and
Each $R_5$ and $R_6$ is independently H, an optionally substituted aliphatic, an optionally substituted heteroaliphatic, an optionally substituted heteroaryl, an optionally substituted phenyl, an optionally substituted aralkyl or an optionally substituted heteroarylalkyl, or
$R_5$ and the adjacent $R_6$ taken together with the atoms to which they are attached form a 5- to 7-membered, optionally substituted monocyclic heterocycle, or a 6- to 12-membered, optionally substituted bicyclic heterocycle, in which each heterocycle ring optionally contains an additional heteroatom selected from —O—, —S— or —$NR_4$—; and Each $R_7$ is independently H, an optionally substituted aliphatic, an optionally substituted heteroaliphatic, an optionally substituted heteroaryl, or an optionally substituted phenyl.

In some embodiments, $R_1$ is P3-L2-P2 which is represented by the structure:

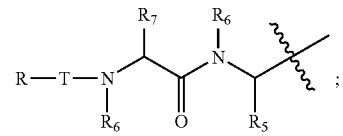

In some embodiments, $R_3$ is P4-L3-P3-L2-P2 which is represented by the structure:

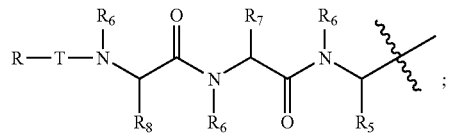

wherein
Each T is independently a bond, H, —C(O)—, —O—C(O)—, —NHC(O)—, —C(O)C(O)— or —$SO_2$—;
Each R is independently H, an optionally substituted aliphatic, an optionally substituted heteroaliphatic, an optionally substituted cycloaliphatic, an optionally substituted heterocyclic, an optionally substituted aralkyl, an optionally substituted heteroaralkyl, an optionally substituted aryl or an optionally substituted heteroaryl;
Each $R_5$, $R_6$, $R_7$ and $R_8$ is independently H, an optionally substituted aliphatic, an optionally substituted heteroaliphatic, an optionally substituted heteroaryl, an optionally substituted phenyl, an optionally substituted aralkyl or an optionally substituted heteroarylalkyl, or
$R_5$ and the adjacent $R_6$ taken together with the atoms to which they are attached form a 5 to 7 membered, optionally substituted monocyclic heterocycle, or a 6 to 12 membered, optionally substituted bicyclic heterocycle, in which each heterocycle ring optionally contains an additional heteroatom selected from —O—, —S— or —$NR_4$—; and each $R_7$ is independently H, an optionally substituted aliphatic, an optionally substituted heteroaliphatic, an optionally substituted heteroaryl, or an optionally substituted phenyl;
$R_7$ and the adjacent $R_6$ together with the atoms to which they are attached may form a 5 to 7 membered, optionally substituted monocyclic heterocycle, a 5 to 7 membered, optionally substituted monocyclic aryl, a 6 to 12 membered, optionally substituted bicyclic heterocycle, or a 6 to 12 membered, optionally substituted bicyclic aryl, in which each heterocycle or aryl ring optionally contains an additional heteroatom selected from —O—, —S— or —NR$_4$—;

R$_8$ and the adjacent R$_6$ together with the atoms to which they are attached may form a 5 to 7 membered, optionally substituted monocyclic heterocycle, a 5 to 7 membered, optionally substituted monocyclic heteroaryl, a 6 to 12 membered, optionally substituted bicyclic heterocycle, or a 6 to 12 membered, optionally substituted bicyclic heteroaryl, in which each heterocycle or heteroaryl ring optionally contains an additional heteroatom selected from —O—, —S— or —NR$_4$—;

R$_8$ and R together with the atoms to which they are attached may form a 5 to 7 membered, optionally substituted monocyclic heterocycle, a 5 to 7 membered, optionally substituted monocyclic aryl, a 6 to 12 membered, optionally substituted bicyclic heterocycle, or a 6 to 12 membered, optionally substituted bicyclic aryl, in which each heterocycle or aryl ring optionally contains an additional heteroatom selected from —O—, —S— or —NR$_4$—;

when R$_5$ and R$_6$ together with the atoms to which they are attached form a ring, R$_7$ and the ring system formed by R$_5$ and R$_6$ may form an 8- to 14-membered optionally substituted bicyclic fused ring system, wherein the bicyclic fused ring system is optionally further fused with an optionally substituted phenyl to form an optionally substituted 10- to 16-membered tricyclic fused ring system.

An example of the HCV protease inhibitors of Formula 2 is the compound of Formula 3 shown below.

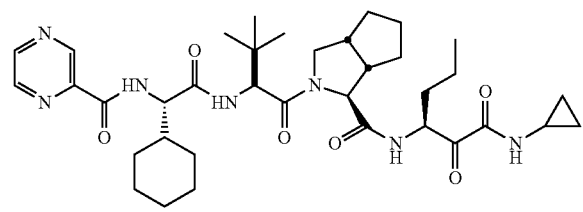

3

In one aspect, the invention provides processes and intermediates for producing an α-hydroxy-β-amino acid derivative of Formula 1, which is useful in producing protease inhibitors:

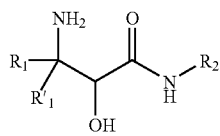

1 wherein R$_1$ and R'$_1$, are each independently H, optionally substituted aliphatic, optionally substituted cycloaliphatic, optionally substituted arylaliphatic, optionally substituted heteroaliphatic or optionally substituted heteroarylaliphatic and R$_2$ is H, optionally substituted aliphatic, optionally substituted cycloaliphatic, optionally substituted arylaliphatic, optionally substituted heteroaliphatic or optionally substituted heteroarylaliphatic and the amino-alcohol amide of Formula 1 has an enantiomeric excess (ee) of greater than 55% (for the definition of ee see, e.g., Jerry March, *Advanced Organic Chemistry, John Wiley and Sons, Inc.*, 1992, p. 125).

In one embodiment, the invention provides a process and intermediates for preparing a compound of Formula 1 as outlined in Scheme 1.

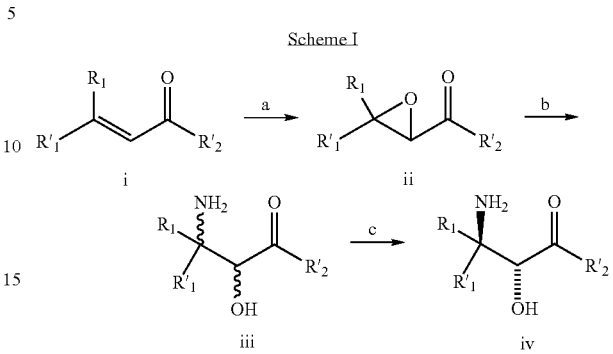

Scheme I

Referring to Scheme I, R$_1$ and R'$_1$ are as previously described; R'$_2$ is —NHR$_2$ or —OE wherein R$_2$ is as previously described and E is C$_1$-C$_5$ alkyl or optionally substituted benzyl. The unsaturated compound i is converted the epoxide ii (step a) using known methods, e.g., oxidation with a peracid such as, for example, meta-chlorperbenzoic acid or peracetic acid (see, e.g., R. S. Porto, M. L. A. A. Vasconcellos, E. Ventura, F. Coelho, *Synthesis*, 2005, 2297-2306), hydrogen peroxide (see, e.g., Dorothee Felix, Claude Wintner, and A. Eschenmoser, Organic Synthesis, Collective Volume 6, p. 679), urea-hydrogen peroxide (also called urea hydroperoxide) in the presence of trifluoroacetic anhydride, Oxone® (KHSO$_5$, potassium peroxomonosulfate) or an organic peroxide such as, for example, tert-butyl hydroperoxide. Alternatively, the epoxide ii may be obtained by using a glycidic ester condensation (see, e.g., M. Ballester, *Chem. Revs.* 55, 283-300 (1955); D. M. Burness, Organic Synthesis, Collective Volume 4, p. 649).

In some embodiments, the epoxidation may be performed to provide optically enriched epoxides (see, e.g., H. Kakei, R. Tsuji, T. Ohshima, M. Shibasaki, *J. Am. Chem. Soc.*, 2005, 127, 8962-8963; M. Marigo, J. Franzen, T. B. Poulsen, W. Zhuang, K. A. Jorgensen, *J. Am. Chem. Soc.*, 2005, 127, 6284-6289; M. Shibisaki, et. al., U.S. Pat. No. 6,833,442 (BINOL Ars complex); R. Kino, K. Daikai, T. Kawanami, H. Furuno, J. Inanaga, *Org. Biomol. Chem.*, 2004, 2, 1822-1824; Y. Shi, U.S. Pat. No. 6,348,608 (OXONE, EDTA, optically active ketone))

The epoxidation step may be conducted on either an ester (R'$_2$=—OE) or on an amide (R'$_2$ =—NHR$_2$). When the epoxidation step is performed on an ester, the ester is subsequently converted to an amide. It is within the scope of the invention that formation of the amide can be performed at any stage of the process using known methods and protecting groups where appropriate.

Reaction of the epoxide ii with a suitable amination reagent (step b) provides the amino alcohol 3. Suitable amination reagents are those which may be converted to the amino compound iii. Examples of suitable amination reagents include azide, phthalimide and an optionally substituted benzyl amine.

In step c, the mixture of amino alcohols of Formula iii is resolved to provide the optically active compound of Formula iv. Suitable methods for resolving the mixture iii include, for example, formation of a salt with a suitable optically active organic acid. Suitable optically active organic acids include, but are not limited to, tartaric acid, malic acid, di-isopropylidenegulonic acid and deoxycholic acid.

In one embodiment, $R'_2$ of Formula i is —$NHR_2$.

In one embodiment, the epoxidation of i is performed using tert-butyl hydroperoxide in the presence of a base such as, for example, sodium hydroxide or butyl lithium.

In another embodiment, the epoxidation is performed using potassium monopersulfate, ethylenediamine tetraacetic acid and an optionally optically active ketone.

In one embodiment, the amino-alcohol of Formula iii has a trans configuration.

In one embodiment, the compound of Formula iv has a 2-(S), 3(S) configuration.

In one embodiment, the amination of ii to give the amino alcohol iii is performed by reaction of ii with sodium azide followed by reduction of the intermediate azide with hydrogen in the presence of a palladium on carbon catalyst.

In another embodiment, the resolution of iii to iv is performed by forming a salt with an optically active acid and crystallizing the thus obtained salt.

In another embodiment, the optically active organic acid is tartaric acid.

In a further embodiment, the optically active organic acid is deoxycholic acid.

In one embodiment, $R_1$ is $C_1$-$C_6$ alkyl and $R'_1$ is H.

In another embodiment, $R_2$ is $C_1$-$C_6$ alkyl or $C_1$-$C_6$ cycloalkyl.

In another embodiment, $R_2$ is cyclopropyl.

In another embodiment, the amino-hydroxy compounds of formula iii may be prepared according to methods described in U.S. Pat. Nos. 6,020,518, 6,087,530 and 6,639,094, each of which is incorporated herein in its entirety by reference.

In another embodiment, as illustrated in Scheme II, this invention provides a process and intermediates for preparing a compound of Formula 3.

Scheme II

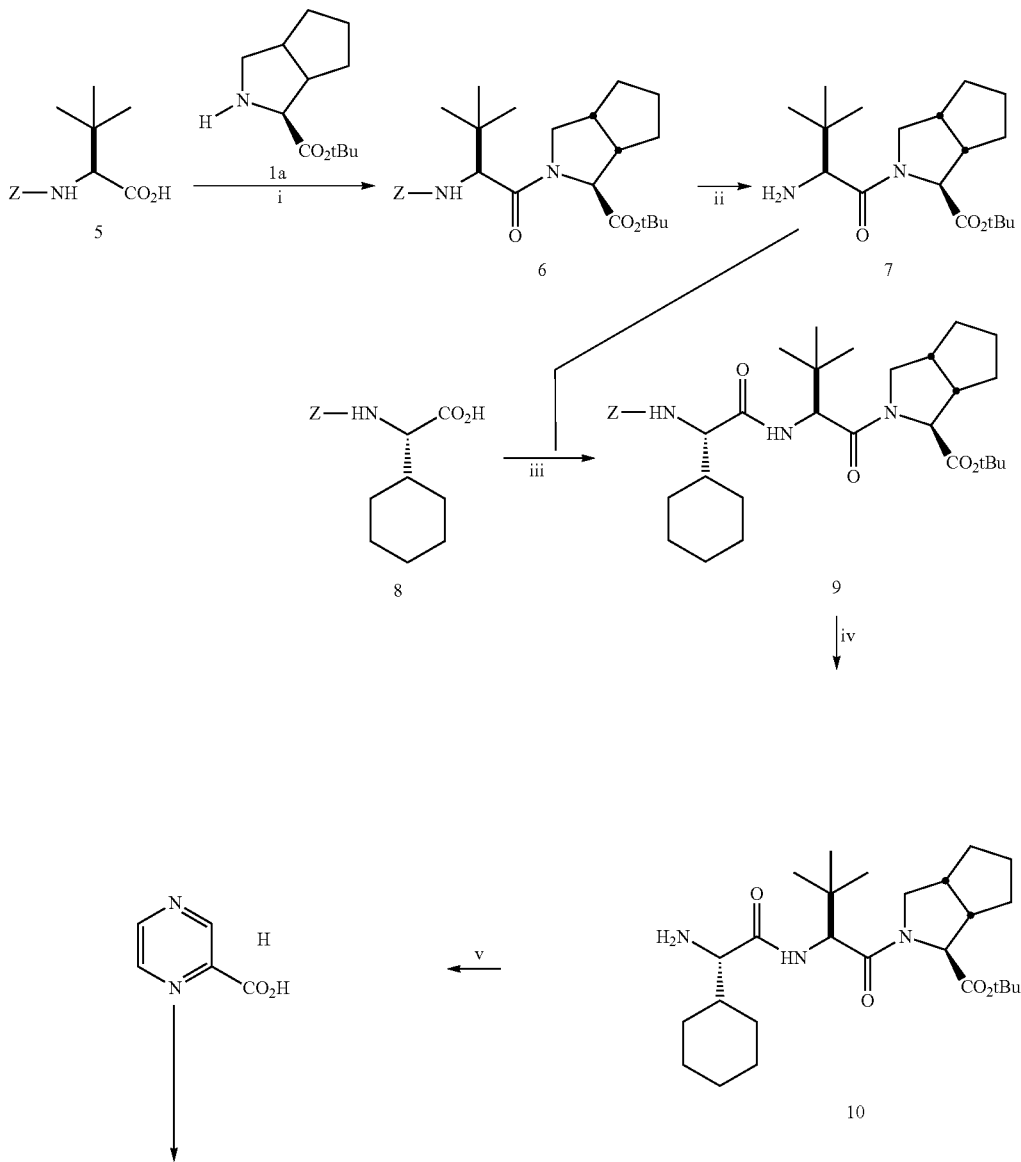

-continued

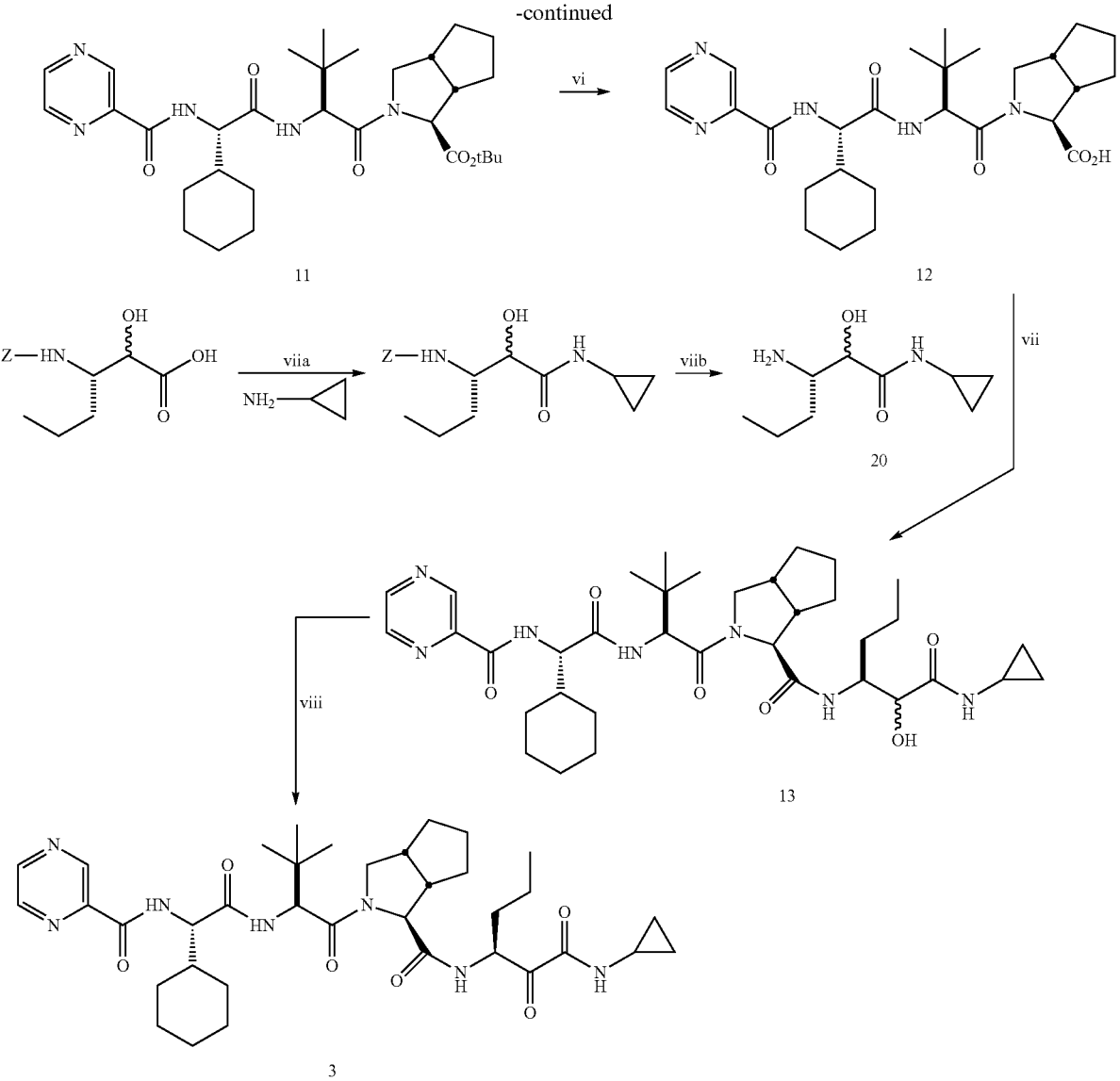

In Scheme II, the bicyclic aminoester of formula 1a is reacted with a protected amino acid of Formula 5, wherein Z is an amine protecting group which can be removed under acidic, basic or hydrogenating conditions different from those used for removing an $R_1$ protecting group, in the presence of a coupling reagent to give an amide-ester of Formula 6. The protecting group Z is removed from the amide-ester of Formula 6 to give the amine-ester compound of Formula 7.

Reacting the amino compound of Formula 7 with the protected amino acid 8 in the presence of a coupling reagent gives the tripeptide of Formula 9.

Removing the protecting group Z in the tripeptide of Formula 9 provides the free amino-tripeptide of Formula 10.

Reacting the amino-tripeptide of Formula 10 with pyrazine-2-carboxylic acid in the presence of a coupling reagent yields the amide-tripeptide ester of Formula 11.

Hydrolysis of the ester of the amide-tripeptide ester of Formula 11 provides the amide-tripeptide acid of Formula 12.

Reacting the amide-tripeptide acid of Formula 12 with the amino-hydroxy amide of Formula 20 in the presence of a coupling reagent gives the hydroxy-peptide of Formula 13.

In the final step, oxidation of the hydroxy group of Formula 12 provides the compound of Formula 3.

Any of the intermediates obtained as described herein, may be used with or without isolation from the reaction mixture. The desired protease inhibitor may be derived by attaching the appropriate $P_2$, $P_2$—$P_3$, or $P_2$—$P_3$—$P_4$ moiety. A coupling of an amine with such a moiety may be carried out using the corresponding carboxylic acid, or reactive equivalent thereof, under standard amide bond-forming or coupling conditions. A typical coupling reaction includes a suitable solvent, the amine in a concentration ranging from about 0.01 to 10M, preferably about 0.1 to 1.0M, the requisite carboxylic acid, a base and a peptide coupling reagent.

If an amine is used without isolation, the coupling may be carried out in situ in the solvent of the reaction mixture used in the preparation of the amine, or in a different solvent. To this reaction mixture, the requisite carboxylic acid may be added and the reaction maintained at a temperature in the range of about 0 to 100° C., preferably between about 20 to about 40° C. The base and peptide coupling reagent are then added to the mixture, which is maintained at a temperature in the range of from about 0 to about 60° C., preferably between about 20 to about 40° C. The base is typically a tertiary amine base, such as triethylamine, diisopropylethylamine, N-methylmorpholine, DBU, DBN, N-methylimidazole, preferably triethylamine or diisopropylethylamine. The amount of base used is generally up to about 20 equivalents per equivalent of the amine, preferably at least about 3 equivalents of base. Examples of peptide coupling reagents include DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O-(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). EDC, HOAT, BOP-Cl and PyBrOP are preferred peptide coupling reagents. The amount of peptide coupling reagent is in the range of about 1.0 to about 10.0 equivalents. Optional reagents that may be used in the amide bond-forming reaction include DMAP (4-dimethylaminopyridine) or active ester reagents, such as HOBT (1-hydroxybenzotriazole), HOAT (hydroxyazabenzotriazole), HOSu (hydroxysuccinimide), HONB (endo-N-hydroxy-5-norbornene-2,3-dicarboxamide), in amounts ranging from about 1.0 to about 10.0 equivalents.

Alternatively, one may treat an amine with a reactive equivalent of the $R_1$ carboxylic acid, such as $P_2$—, $P_3$—$P_2$—, or $P_4$—$P_3$—$P_2$—C(=O)$X^1$, where —C(=O)$X^1$ is a group that is more reactive than COOH in the coupling reaction. Examples of —C(=O)$X^1$ groups include groups where $X^1$ is Cl, F, OC(=O)R(R=aliphatic or aryl), —SH, —SR, —SAr, or —SeAr. Acid and amine protecting groups as used herein are known in the art (see, e.g., T. W. Greene & P. G. M Wutz, *Protective Groups in Organic Synthesis*, 3$^{rd}$ Edition, John Wiley & Sons, Inc. (1999) and the earlier editions of this book).

A number of chemical groups are known that may be used as the $P_3$—$P_2$— portion of the protease inhibitor. Examples of such $P_3$—$P_2$— groups are included in U.S. Application No. 60/709,964, which is also incorporated hereto by reference in its entirety.

Other methods well known in the art may also be used to implement the methods of this invention and even to make the compounds of this invention. See, e.g., WO 07/022,459 A2, which is incorporated herein by reference in its entirety.

III. EXAMPLES

The following examples are for the purpose of illustration only and are not to be construed as limiting the scope of the invention in any way.

Example 1

3-Propyloxirane-2-carboxylic acid

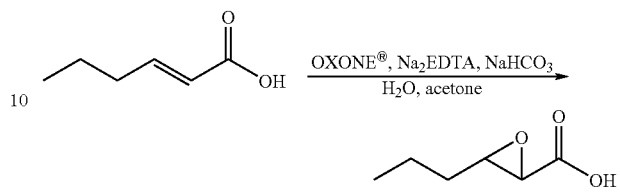

A flask equipped with an overhead stirrer, thermometer and addition funnel was placed under a nitrogen atmosphere then charged with trans-2-hexenoic acid (69.8 g, 611 mmol), water (420 mL) and acetone (420 mL). Sodium bicarbonate (NaHCO$_3$, 224 g, 2.66 mol) was then added portion-wise keeping the reaction temperature at 25±5° C. Once all of the sodium bicarbonate had been added, a solution of OXONE® (454 g, 738 mmol) in 4×10$^{-4}$ M ethylenediaminetetraacetic acid disodium salt dehydrate (Na$_2$EDTA; 1.32 L) was charged to the addition funnel and added over 90 minutes keeping the reaction temperature at 25±5° C. and the pH between 9.5 and 7.5. The reaction mixture was then allowed to stir for 16 h, after which time no (E)-hex-2-enoic acid was observed by HPLC analysis. The mixture was cooled to 0±5° C., acidified to pH 2 with 6 N HCl (515 mL, 2.8 mol) and extracted with ethyl acetate (EtOAc; 3×250 mL). The combined organic phases were dried over sodium sulfate (Na$_2$SO$_4$), filtered then concentrated under reduced pressure to provide the title compound (60.4 g, 76%) as a yellow oil.

$^1$H NMR (500 MHz, d$_6$-DMSO) δ12.88 (br s, 1 H), 3.21 (s, 1 H), 3.06-3.03 (m, 1 H), 1.58-1.36 (m, 4 H), 0.91 (t, J=7.5 Hz, 3 H).

Example 2

N-cyclopropyl-3-propyloxirane-2-carboxamide

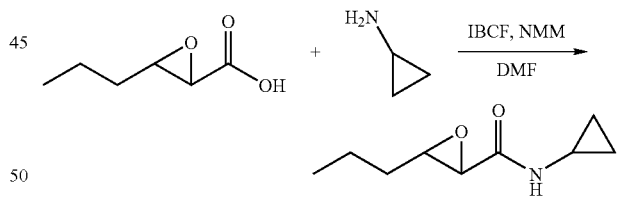

A flask equipped with an overhead stirrer, thermometer and addition funnel was placed under a nitrogen atmosphere then charged with the acid of Example 1 (20.0 g, 154 mmol), and isopropyl acetate (IPAc; 200 mL) then cooled to 0±5° C. 4-Methylmorpholine (NMM, 154 mL, 17 mL) was charged to the addition funnel then added maintaining the temperature at 0±5° C. Once addition was complete the addition funnel washed with IPAc (10 mL) and then charged with isobutyl chloroformate (IBCF, 137 mmol, 19.5 mL) which was added keeping the temperature at 0±5° C. The reaction mixture was stirred at 0±5° C. for 90 min after which time a solution of cyclopropylamine (154 mmol, 10.7) in IPAc (80 mL) was added keeping the temperature at 0±5° C. Upon completion of addition the reaction was warmed to 25±5° C. and allowed to stir for 18 h. Sodium hydroxide (231 mL, 1.0 N) was added and the biphasic mixture stirred vigorously for 30 min, then the layers were separated. The organic phase was then washed with HCl (231 mL, 1.0 N). The combined organic phases were dried over sodium sulfate (Na$_2$SO$_4$), filtered and concentrated under reduced pressure to provide the title compound (19.5 g, 75%) as an orange oil.

$^1$H NMR (500 MHz, d$_6$-DMSO) 7.97 (bs, 1 H), 3.10 (d, J=1.9 Hz, 1 H), 2.99-2.95 (m, 1 H), 2.67-2.61 (m, 1 H), 1.60-1.36 (m, 4 H), 0.90 (t, J=7.3 Hz, 3 H), 0.62-0.58 (m, 2 H), 0.47-0.43 (m, 2 H)

Example 3

Alternate preparation of
N-cyclopropyl-3-propyloxirane-2-carboxamide

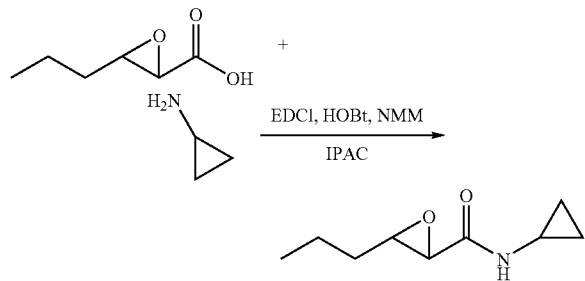

A flask equipped with a stir bar, thermometer and addition funnel was placed under a nitrogen atmosphere then charged with the acid of Example 1 (5.0 g, 38 mmol), N-(3-dimethylaminopropyl)-N'-ethylcarbodiimide hydrochloride (EDCI; 8.1 g, 42 mmol), 1-hydroxybenzotriazole hydrate (HOBt; 5.7 g, 42 mmol) and N,N-dimethylformamide (DMF; 50 mL) then cooled to 0±5° C. The addition funnel was charged with NMM (5.9 mL, 54 mmol) which was then added to the reaction mixture maintaining the temperature at 0±5° C. The mixture was stirred for 30 minutes then cyclopropylamine (2.9 mL, 42 mmol) was added and the reaction allowed to warm to 25±5° C. over 16 hours. Hydrochloric acid (50 mL, 1.0 N) and IPAc (50 mL) were added and then the mixture stirred for an additional 30 minutes. The contents were transferred to separatory funnel, the layers separated then the organic layer was washed sequentially with HCl (50 mL, 1.0 N), saturated aqueous NaHCO$_3$ (2×50 mL), and brine (2×50 mL). The combined organic phases were dried over sodium sulfate (Na$_2$SO$_4$), filtered then concentrated under reduced pressure to provide title amide (3.2 g, 50%) as an orange oil.

Example 4

Trans-N-cyclopropyl-2-hexenamide

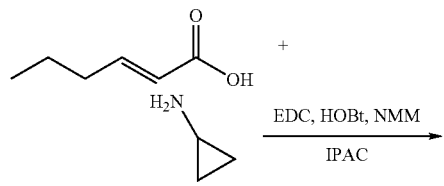

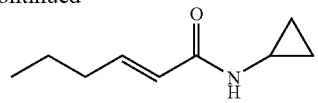

A flask equipped with an overhead stirred, thermometer and addition funnel was placed under a nitrogen atmosphere then charged with (E)-hex-2-enoic acid (89.8 g, 787 mmol), EDCI (158.3 g, 826 mmol), HOBt (112.0 g, 826 mmol) and IPAc (890 mL) then cooled to 0±5° C. The addition funnel was charged with NMM (99.1 mL, 1.6 mol) which was then added to the reaction mixture maintaining the temperature at 0±5° C. The mixture was stirred for 30 minutes then cyclopropylamine (60.0 mL, 866 mmol) was added and the reaction allowed to warm to 25±5° C. over 16 hours. The reaction mixture was washed by adding hydrochloric acid (500 mL, 1.0 N) and the mixture stirred vigorously for 30 minutes then allowed to sit for 30 minutes; the layers were separated and the washing procedure repeated. Sodium hydroxide (500 mL, 1.0 N) was added and then the mixture stirred vigorously for 30 minutes then allowed to sit for 30 minutes; the layers were separated and base wash procedure repeated. Water (500 mL) was added and then the mixture stirred vigorously for 30 minutes then allowed to sit for 30 minutes; the layers were separated and the wash procedure repeated. The combined organic phases were concentrated under reduced pressure to ⅓ original volume then IPAc (600 mL) was added; this was repeated two times when a white precipitate formed. The slurry was then concentrated under atmospheric pressure to ⅔ original volume then cooled to 50±5° C. N-heptane (890 mL) was slowly added while the reaction was cooled to −5±5° C. and held at this temperature for 4 hours. The solid was filtered, washed with cold n-heptane (2×250 mL) and dried to provide the title amide (82.4 g, 68%) as a fine white solid.

$^1$H NMR (500 MHz, d$_6$-DMSO) 7.89 (s, 1 H), 6.58 (dt, J=15.2, 7.0 Hz, 1 H), 5.80 (dt, J=15.2, 1.3 Hz, 1 H), 2.70-2.65 (m, 1 H), 2.12-2.06 (m, 2 H), 1.44-1.37 (m, 2 H), 0.88 (t, J=7.3 Hz, 3 H), 0.64-0.60 (m, 2 H), 0.42-0.38 (m, 2 H).

Example 5

N-cyclopropyl-3-propyloxirane-2-carboxamide

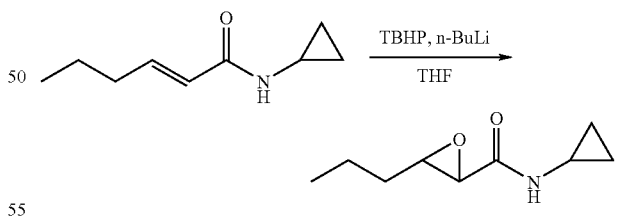

A flask equipped with an overhead stirrer, thermometer and addition funnel was placed under a nitrogen atmosphere then charged with tert-butyl hydrogen peroxide (TBHP; 95 mL, 5.5 M, 522 mmol) and tetrahydrofuran (THF; 200 mL). The reaction was cooled to −20±5° C. and n-butyl lithium (n-BuLi; 235 mL, 2.5 M, 587 mmol) was charged to the addition funnel and slowly added, keeping the reaction temperature below −5±5° C. Upon completion of addition the reaction was warmed to 0±5° C. and the amide of Example 4 (19.80 g, 130 mmol) in THF (20 mL) was added maintaining the temperature at 0±5° C. after which the temperature was increased to 25±5° C. and the reaction stirred for 12 hours. After this time IPAc (200 mL) and saturated aqueous sodium hydrosulfite (200 mL) were added and the reaction stirred for 60 min. The layers were separated and the aqueous layer extracted with IPAc (twice, 75 mL each). The combined organic phases were dried over sodium sulfate (Na$_2$SO$_4$), filtered and concentrated under reduced pressure to provide the title compound (21.87 g, 99%).

Example 6

N-cyclopropyl-3-propyloxirane-2-carboxamide

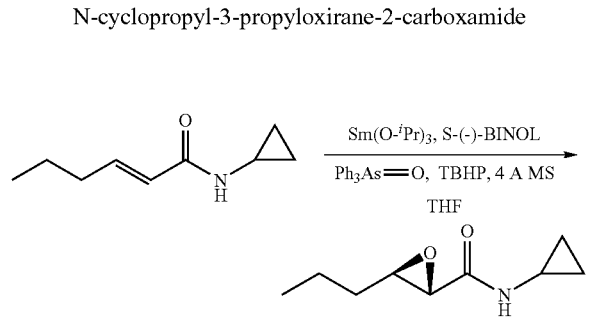

A flask equipped with a stir bar, thermometer and addition funnel was placed under a nitrogen atmosphere then charged with samarium (III) isopropoxide (Sm(O-i-Pr)$_3$, 430 mg, 1.3 mmol), triphenyl arsine oxide (Ph$_3$As=O; 420 mg, 1.3 mmol), S-(−)1,1'-bi-2-naphthol ((S)-BINOL), 370 mg, 1.3 mmol), 4 Å molecular sieves (13 g) and THF (20 mL) then stirred for 30 min at 25±5° C. Tert-butyl hydroperoxide (2.8 mL, 5.5 M, 16 mmol) was then added. The mixture stirred for 30 minutes at 25±5° C., the amide of Example 4 (2.0 g, 13 mmol) in THF (2.0 mL) was then added. The reaction was stirred for 14 hours after which time the reaction had reached 95% completion as determined by HPLC.

Example 7

N-cyclopropyl-3-propyloxirane-2-carboxamide

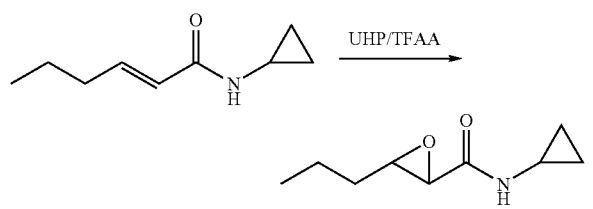

To a three-neck 250 mL round bottom flask equipped with mechanical stirrer and containing (E)-N-cyclopropylhex-2-enamide (10.0 g, 65.3 mmole) and urea hydrogen peroxide (UHP) (25.0 g, 4.0 eq.) in CH$_2$Cl$_2$ (100 mL, 10 vol) at 0° C., was added trifluoroacetic anhydride (41.1 g, 27.2 mL, 3.0 eq.). The reaction mixture was heated to 35±5° C. and stirred for 2 hours. After cooling the reaction mixture down to room temperature, another aliquot of trifluoroacetic anhydride (13.7 g, 9.0 mL, 1.0 eq.) was added. The reaction mixture was heated again to 35±5° C. and stirred for another 3 hours.

The reaction mixture was then again cooled to 0° C. and quenched by adding saturated NaHCO$_3$ (5 vol.) slowly and stirring for 30 minutes. The organic layer was separated, and the aqueous layer was extracted with CH$_2$Cl$_2$ (50 mL, 5 vol).

The combined organic layer was dried and evaporated to afford 10.0 g (90%) of the crude the product, N-cyclopropyl-3-propyloxirane-2-carboxamide, as a pale yellow oil. The crude product was used for the next step without further purification.

Example 8

3-Azido-N-cyclopropyl-2-hydroxyhexanamide

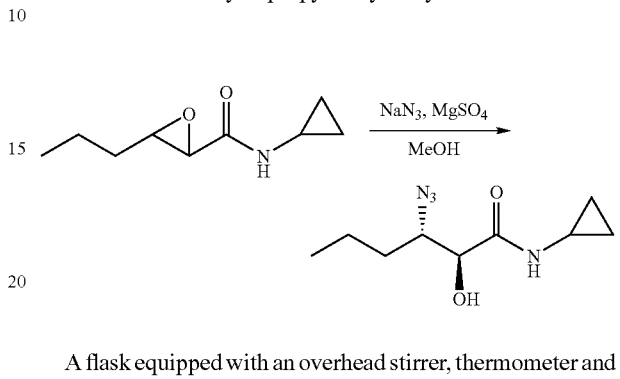

A flask equipped with an overhead stirrer, thermometer and reflux condenser was placed under a nitrogen atmosphere then charged with the epoxide of Example 5 (20.0 g, 118 mmol), sodium azide (NaN$_3$; 31.0 g, 473 mmol), magnesium sulfate (MgSO$_4$; 14.0 g, 118 mmol) and methanol (MeOH; 200 mL). The mixture was heated to 65±5° C. for 2 hours then cooled to 25±5° C. and filtered through a pad of Celite 545. The solvent was removed under reduced pressure resulting in a thick oil which was taken up in IPAc (250 mL) then washed with water (3×250 mL). The organic phase was dried over sodium sulfate (Na$_2$SO$_4$), filtered and concentrated under reduced pressure to provide the title compound (15.1 g, 60%) as a white solid.

$^1$H NMR (500 MHz, d$_6$-DMSO) 7.87 (s, 1 H), 5.97 (d, J=6.0, 1 H), 4.02 (dt, J=6.0, 3.8 Hz, 1 H), 2.70-2.65 (m, 1 H), 1.60-1.20 (m, 4 H), 0.88 (t, J=7.0 Hz, 3 H), 0.63-0.58 (m, 2 H), 0.51-0.46 (m, 2 H).

Example 9

3-Amino-N-cyclopropyl-2-hydroxyhexanamide

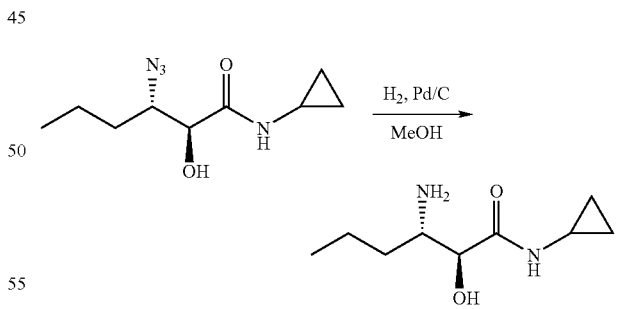

The azide of Example 7 (15.1 g, 71.3 mmol), Pd/C (1.5 g, 5 wt %, 50% wet) and MeOH (150 mL) was charged to a pressure vessel then purged with nitrogen gas for 5 min. The vessel was sealed, pressurized to 1 bar with nitrogen gas then released three times. The same was repeated with hydrogen gas. After the third purge with hydrogen the vessel was charged with 3 bar of hydrogen. Agitation was begun and a temperature of 25±5° C. was maintained. Reaction was stirred in this manner for 14 hours after which time the reaction mixture was filtered through a pad of Celite 545 and the solvent removed to provide crude amino-alcohol (8.48 g) as a yellow solid. To this material was added acetonitrile (ACN; 150 mL) and the reaction heated to reflux at which time all of the solids dissolved. The mixture was then cooled to 25±5° C. and the white needles formed were collected, washed with cold ACN and dried to provide purified amino-alcohol (4.87 g).

$^1$H NMR (500 MHz, d$_6$-DMSO): 8.05 (br s, 3 H), 4.20 (d, J=3.2, 1 H), 3.42-3.34 (m, 1 H), 2.71-2.65 (m, 1 H), 1.51-1.20 (m, 4 H), 1.17 (d, J=6.5 Hz, 1 H), 0.83 (t, J=7.6 Hz, 3 H), 0.64-0.60 (m, 2 H), 0.54-0.49 (m, 2 H).

Example 10

3-Amino-N-cyclopropyl-2-hydroxyhexanamide, L-tartaric acid salt

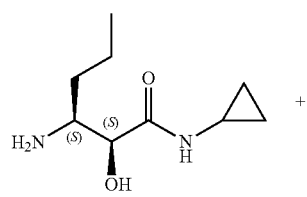

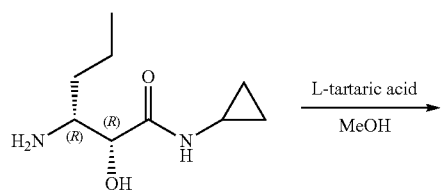

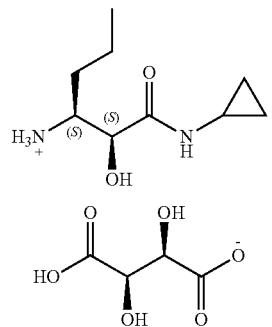

To a racemic mixture of 3-amino-N-cyclopropyl-2-hydroxyhexanamide (100 mg, 0.53 mmol) in MeOH (1 mL) was added L-tartaric acid (39.7 mg, 0.26 mmol) in MeOH (20 µL) and the mixture cooled to 0±5° C. After 48 h at 0±5° C. a white precipitate had formed which was collected, washed with methyl tert-butyl ether (2×5 mL) then dried to provide the title compound. Chiral HPLC analysis and comparison with an authentic sample of the chiral amino-alcohol hydrochloride salt showed that the title compound was obtained with 62 ee %.

Example 11

3-Amino-N-cyclopropyl-2-hydroxyhexanamide, deoxycholic acid salt

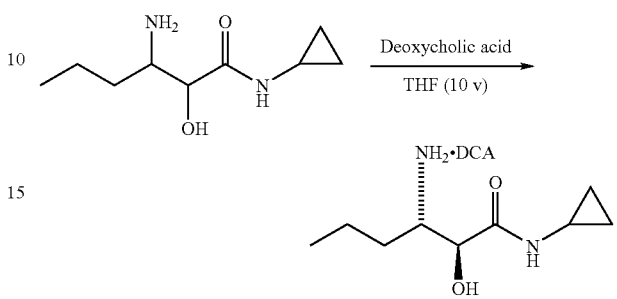

To a three-neck 250 mL round bottom flask equipped with mechanical stirrer and containing the racemic 3-amino-N-cyclopropyl-2-hydroxyhexanamide (10.0 g, 53.69 mmole) in THF (100 mL) was charged deoxycholic acid (15.8 g, 40 27 mmole, 0.75 eq.). The reaction mixture was stirred and heated at 65±5° C. for 2 hours. The resulting homogeneous mixture was allowed to cool to temperatures between 22 and 25° C. over an hour, and it was maintained at the same temperature range for 4 hours. The precipitated solids were collected by filtration, washed with THF (10 mL), dried overnight to give 12.2 g of the deoxycholic acid salt of 3-amino-N-cyclopropyl-2-hydroxyhexanamide (41%, Enantiomeric Ratio(ER)= 3:97) as a white solid.

Example 12

3-Amino-N-cyclopropyl-2-hydroxyhexanamide, hydrochloric acid salt

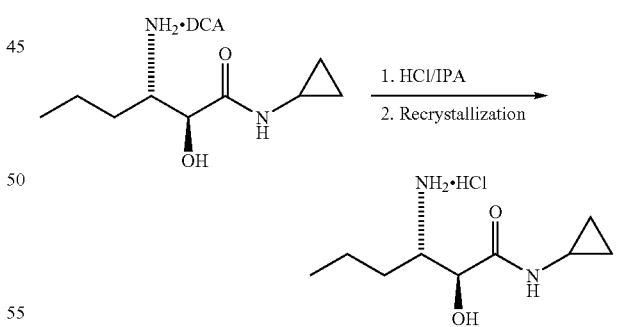

To a three-neck 250 mL round bottom flask equipped with mechanical stirrer and containing the mixture of the deoxycholic salt obtained in Example 11 in 2-propanol (62 mL) was added 5 to 6 N HCl solution in isopropyl alcohol (66 mL, 3 eq.) with stirring. The resulting solution was heated at 75±5° C. for an hour and allowed to cool to temperatures between 22 and 25° C. over 1 hour, and it was maintained at the same temperature range for 2 hours. The precipitated solids were collected by filtration, washed with 2-propanol (12 mL, 1 v), dried overnight to give 7.2 g of 3-amino-N-cyclopropyl-2- hydroxyhexanamide hydrochloric acid salt (75%, Enantiomeric Ratio(ER)=0.05:99.95) as a white solid.

Example 13

Preparation of (1S,3aR,6aS)-2-((S)-2-((S)-2-cyclohexyl-2-(pyrazine-2-carboxamido)acetamido)-3,3-dimethylbutanoyl)-N-((S)-1-(cyclopropylamino)-1,2-dioxo-hexan-3-yl)octahydrocyclopenta[c]pyrrole-1-carboxamide

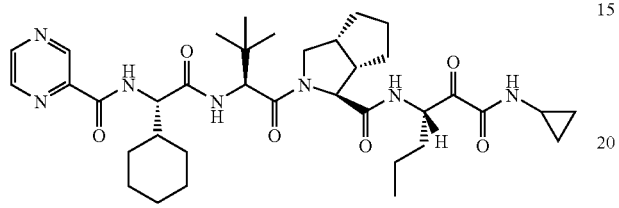

Step a: Preparation of

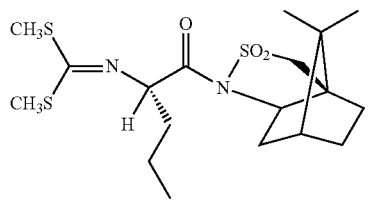

(compound vii shown below)

The sultam shown above vi is prepared by known methods such as those described in Y. Elemes and U. Ragnarsson, *J. of Chem. Soc., Perkin* 1, 1996, 6, p. 537; W. Oppolzer, et. al., *Helv. Chim. Acta.*, 1994, 25: 2363), by using the corresponding unsubstituted sultam and propyl iodide.

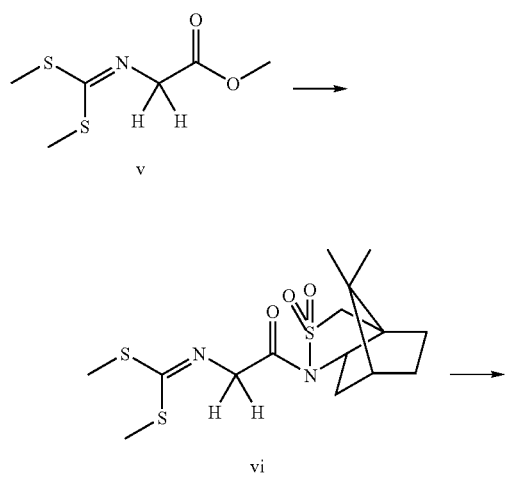

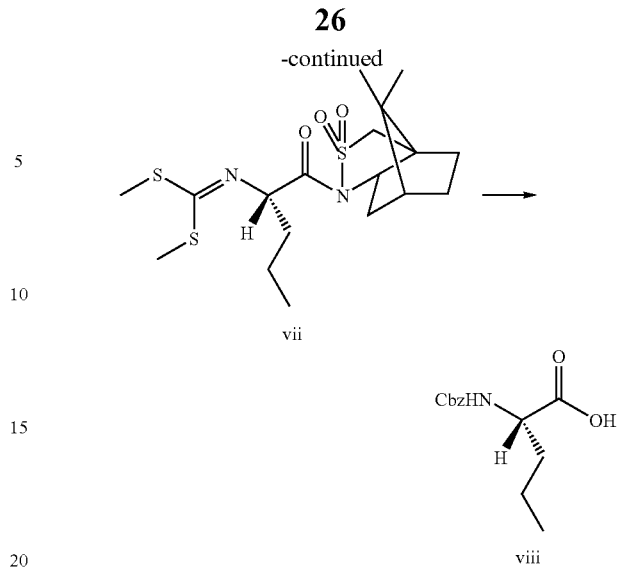

A 500 mL round-bottomed-flask with a magnetic stir bar and N₂ inlet is charged with vi (17.32 g, 45.8 mmol), and THF (229 mL). The resulting solution is cooled to −78° C. and n-BuLi (31.5 mL of a 1.6 M solution in hexane, 50.3 mmol) is added via syringe pump over 1 hour. The resulting yellow solution is aged for 30 minutes and then a solution of HPMA (56 mL) and n-PrI (13.4 mL, 137 mmol) is added over 30 minutes. The mixture is allowed to warm to the room temperature over 8 hours. The mixture is cooled to −20° C. and H₂O (50 mL) is added. The reaction is extracted with EtOAc (400 mL) and the organic phases are dried over MgSO₄ and concentrated to provide 61.3 g of the crude oil. Chromatography on 500 g of silica gel eluting with 2:1 heptane/EtOAc followed by concentration of the rich cut give 20.35 g of a white solid. This is recrystallized from EtOH (210 mL) to give compound vii as a white crystalline solid.

Step b: Preparation of
(S)-2-(benzyloxycarbonylamino)-pentanoic acid
(compound viii shown above)

Compound vii (15.39 g, 32.1 mmol) is combined with THF (100 mL) and 1N HCl (50 mL). The resulting emulsion is stirred overnight at the room temperature and then concentrated under reduced vacuum to provide a thick oil. The oil is dissolved in THF (100 mL), water (25 mL) and LiOH (3.08 g, 128 mmol) is added. The resultant solution is stirred overnight at the room temperature and then concentrated to remove the THF, resulting a hazy light yellow emulsion. The emulsion is diluted with water (25 mL) and extracted with CH₂Cl₂ (3×50 mL). The aqueous phase is diluted with THF (200 mL) and then cooled to 0° C. while stirring rapidly and CBZ-Cl (7.6 mL, 54 mmol) is added dropwise over 15 minutes. After 1 hour at 0° C., the THF is removed in vacuo and the residue is acidified by addition of 50 mL of 1 N HCl. This is extracted with EtOAc (3×100 mL) and the organic phase is dried over Na₂SO₄ and concentrated to provide an oil. The residue is dissolved in EtOAc (25 mL) and heptane (150 mL), seeded and stirred overnight at the room temperature. The solids are collected on a frit, rinsed with heptane (30 mL) and air dried to give compound viii.

Step c: Preparation of (S)-2-(benzyloxycarbonylamino)-pentanoic acid

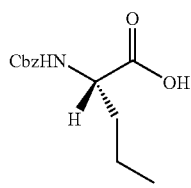

As shown below, the title compound is prepared by hydrolysis of the sultam product of Step a and conversion of the resultant free amino acid to its Cbz derivative by known methods (see, e.g., W. Green, P. G. M. Wuts, Protective Groups in Organic Synthesis, Wiley-Interscience, New York, 1999).

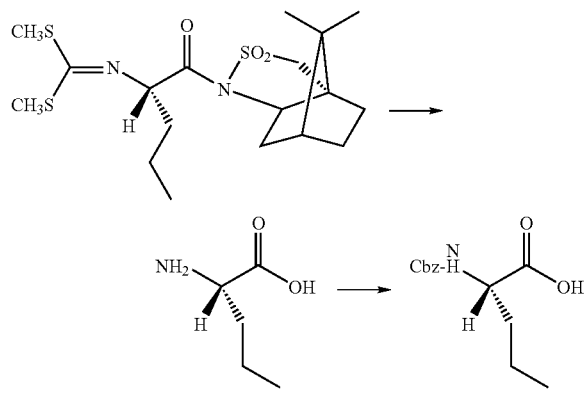

Step d: Preparation of (S)-benzyl 1-(methoxy(methyl)amino)-1-oxo-2-pentan-2-ylcarbamate

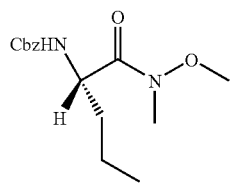 [SMILES: CCC[C@H](NC(=O)OCc1ccccc1)C(=O)N(C)OC]

To a flask containing 1.0 g of (S)-2-(benzyloxycarbonylamino)-pentanoic acid (3.97 mmol) in 20 mL of dichloromethane maintained at 0° C., is added 3.0 eq. of N-methylmorpholine (700 uL), 1.5 eq. of N,O-dimethylhydroxylamine hydrochloride (581 mg) and 1.5 eq. of EDCI (1.14 g). The reaction mixture is stirred overnight from 0° C. to the room temperature. The reaction mixture is then diluted in dichloromethane and washed with HCl (1N) and brine. The organic layer is dried over MgSO$_4$. The crude mixture is purified by flash chromatography (ethyl acetate 15-75% in hexanes) to afford the title compound.

Step e: Preparation of (S)-benzyl 1-oxo-2-pentan-2-ylcarbamate

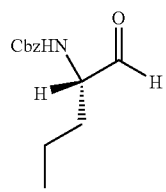 [SMILES: CCC[C@@H](C=O)NC(=O)OCc1ccccc1]

Using procedures described in WO 02/18369, the Cbz-protected amino acid of Step d is converted to the title compound. Specifically, into a flask containing 1.0 eq. of (S)-benzyl 1-(methoxy(methyl)amino)-1-oxo-2-pentan-2-ylcarbamate (810 mg, 2.75 mmol) in 10 mL of dry THF maintained at 0° C. (in an ice bath) is added slowly 1.7 eq. of a solution of lithium borohydride (1.0M) (4.67 mL). After about 10 minutes, the ice bath is removed and the reaction continue for an hour. The reaction solution is quenched at 0° C. by adding 5 mL of a solution of KHSO$_4$ (10%). The solution is then diluted by the addition of 10 mL of HCl (1N). The mixture is stirred for 30 minutes, then extracted 3 times with dichloromethane. The organic phases are combined and washed with a solution of HCl (1 N), water and brine. The organic phase is then dried over MgSO$_4$ and the volatile evaporates. The aldehyde is used as is in the next step.

Step f: Preparation of benzyl (3S)-1-(cyclopropylamino)-2-hydroxy-1-oxo-hexan-3-ylcarbamate

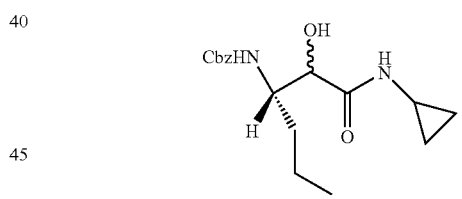

Cyclopropyl isocyanide is prepared according to the scheme shown below.

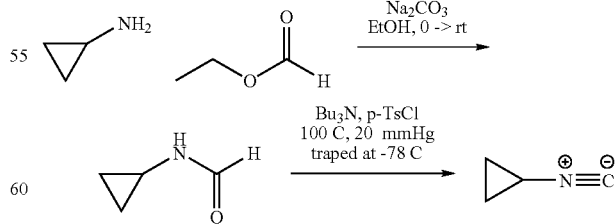

Specifically, the cyclopropyl isonitrile is coupled with the aldehyde product of Step d to give the title compound as described in J. E. Semple et al., Org. Lett., 2000, 2 (18), 2769; Lumma W., J. Org. Chem., 1981, 46, 3668.

Step g: Preparation of (3S)-3-amino-N-cyclopropyl-2-hydroxyhexanamide

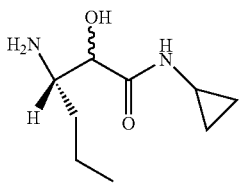

Hydrogenolysis of the Cbz compound of Step e is achieved by using a palladium on carbon catalyst in the presence of hydrogen to give the title compound. Shown in the following schemes are Steps d, e, f, and g.

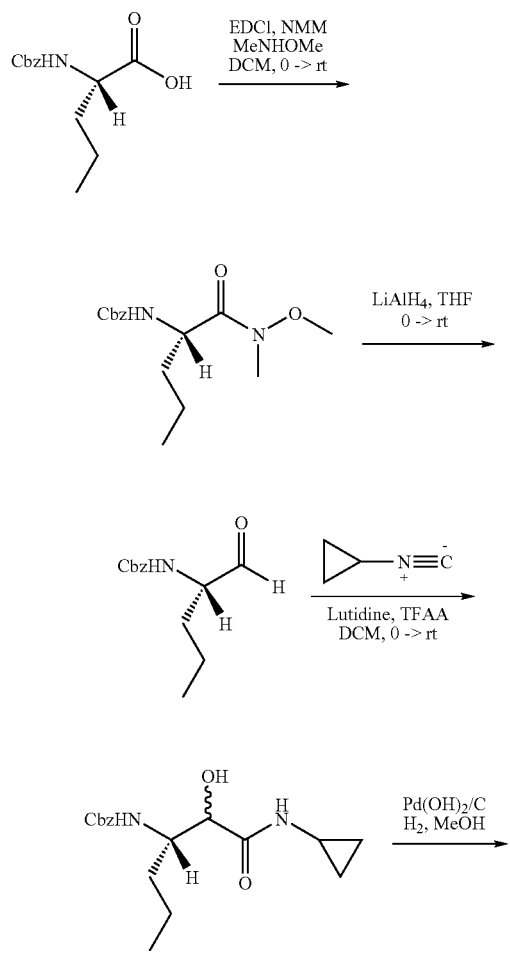

Step h: Preparation of (1S,3aR,6aS)-2-((S)-2-((S)-2-cyclohexyl-2-(pyrazine-2-carboxamido)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide

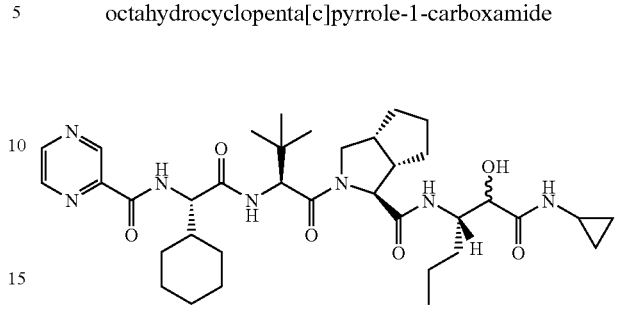

The title compound is prepared from the hydroxy-amino amide product of Step g by condensation with the appropriate acid in the presence of a coupling reagent such as, e.g., EDCI and HOSu. Specifically, in a flask containing 1.2 eq. of (1S,3aR,6aS)-2-((S)-2-((S)-2-cyclohexyl-2-(pyrazine-2-carboxamido)acetamido)-3,3-dimethylbutanoyl)octahydrocyclopenta[c]pyrrole-1-carboxylic acid (1.59 g) in 20 mL of DMF, is added 2.5 eq. of diisopropylamine (980 uL), 1.2 eq. N-hydroxybenzotriazole hydrate (411 mg) and 1.3 eq. of EDCI (558 mg). After 15 minutes of stirring at the room temperature, 1.0 eq. of (3S)-3-amino-N-cyclopropyl-2-hydroxyhexanamide hydrochloride (500 mg) is added to the mixture. After another 24 hours, the reaction mixture is diluted into 400 mL of ethyl acetate. The organic phase of the mixture is washed with HCl (1N), water, saturated sodium bicarbonate solution, brine, and then dried over MgSO$_4$. The crude product is purified by chromatography on silica (ethyl acetate 70-100% in Hexanes) to give the tile compound.

Step i: Preparation of (1S,3aR,6aS)-2-((S)-2-((S)-2-cyclohexyl-2-(pyrazine-2-carboxamido)acetamido)-3,3-dimethylbutanoyl)-N-((S)-1-(cyclopropylamino)-1,2-dioxo-hexan-3-yl)octahydrocyclopenta[c]pyrrole-1-carboxamide

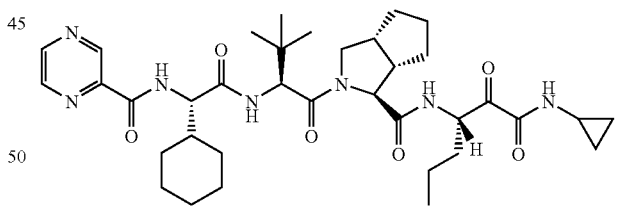

The title compound is prepared by oxidation of the product of Step h with a suitable oxidizing reagent such as Dess-Martin periodinane or TEMPO and sodium hypochlorite. Specifically, in a flask containing 1.31 g of (1S,3aR,6aS)-2-((S)-2-((S)-2-cyclohexyl-2-(pyrazine-2-carboxamido)acetamido)-3,3-dimethylbutanoyl)-N-((3S)-1-(cyclopropylamino)-2-hydroxy-1-oxohexan-3-yl)octahydrocyclopenta[c]pyrrole-1-carboxamide in 40 mL of dichloromethane is added at room temperature 1.06 g of Dess-Martin periodinane. After 2 hours of stirring, 50 mL of sodium bisulfite (1N) is added, and the mixture is stirred for 30 minutes. The 2 phases are separated, the organic is washed with water twice, brine and dried over Na$_2$SO$_4$. The crude product was purified by chromatography on silica (ethyl acetate 20-100% in Hexanes) to give the title compound. The diastereoisome ratio is determined by chiral HPLC normal phase.
The following scheme shows the reactions of both Steps g and h.
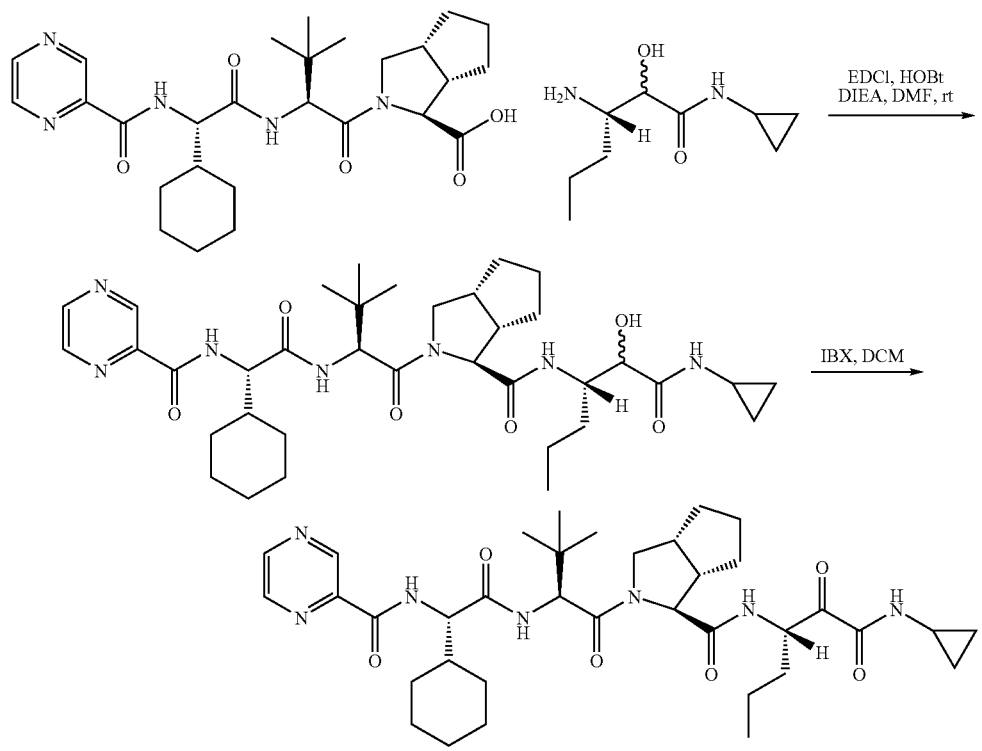
Example 14
Preparation of (2S,3S)-3-amino-N-cyclopropyl-2-hydroxyhexanamide hydrochloride 40
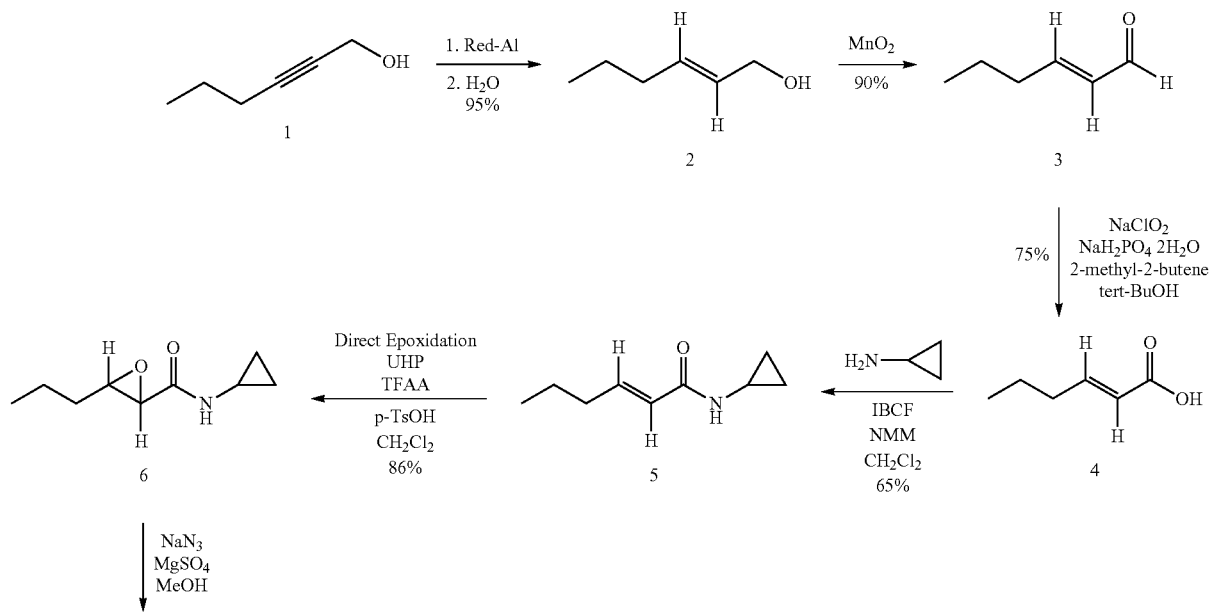

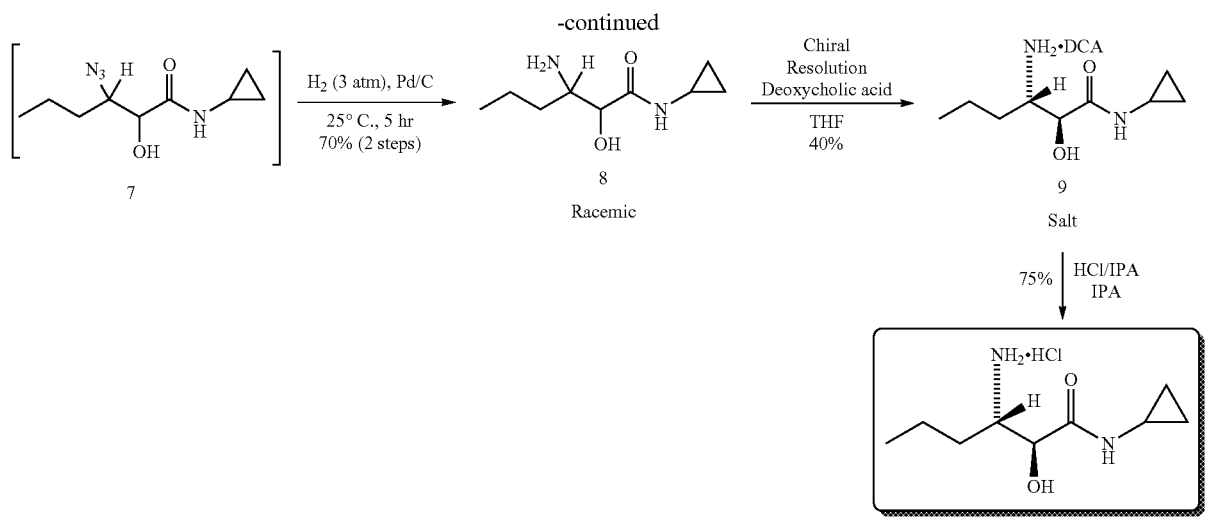

Step 1. Reduction (trans-2-Hexen-1-ol)

To a three-neck 250 mL round bottom flask equipped with mechanical stirrer and reflux condenser is charged 2-hexyn-1-ol (10 g, 0.1 mole) and THF (100 mL, 10 vol). The resulting mixture is cooled down to 0±5° C. and then Red-Al (65% in Toluene, 32 mL, 1.6 eq) is added slowly under a nitrogen atmosphere between 0° C. and 20° C. The resulting mixture is allowed to warm to 25° C. and stirred for 5 hours. The reaction mixture is then cooled to −5±5° C. and H$_2$O (8.2 g, 4 eq) is added dropwise between 0° C. and 15° C. To the resulting mixture is charged IPAC (50 mL, 5 vol) and saturated NH$_4$Cl solution (50 mL, 5 vol). After stirring the mixture for 10 minutes, the white solid formed is filtered out. The organic layer from the filtrate is separated and the aqueous layer extracted with IPAC (30 mL, 3 vol). The organic layers are combined and washed with water (30 mL, 3 vol) and dried over MgSO$_4$ and concentrated to afford the product, i.e., compound 2. The crude product is used for the next step without further purification.

Step 2. Oxidation: MnO$_2$ (trans-2-Hexen-1-al)

To a three-neck 250 mL round bottom flask equipped with mechanical stirrer containing 2-Hexen-1-ol-3d (10 g, 0.1 mole) in CH$_2$Cl$_2$ (150 mL, 15 vol) is charged activated MnO$_2$ (87 g, 10 eq) at the room temperature. After vigorous stirring for 1 hour, another portion of MnO$_2$ (16 g, 2 eq) is added and the shaking is continued for 4 hours. The reaction solution is filtered through a pad of Celite®. The solvent is removed under vacuo (25° C., 100 mmHg) to give the crude aldehyde product (i.e., compound 3). The crude product is used for the next step without further purification.

Step 3. Oxidation: NaClO$_2$ (trans-2-Hexenoic acid)

To a three-neck 500 mL round bottom flask equipped with mechanical stirrer and reflux condenser is charged 2-hexen-1-al-3d (10 g, 0.1 mole), tert-BuOH (90 mL, 9 vol), and 2-methyl-2-butene (30 mL, 3 vol). The resulting solution is added with a freshly prepared aqueous NaClO$_2$ (27.4 g, 3 eq) and NaH$_2$PO$_4$ (62.9 g, 4 eq) in water (200 mL) over 30 minutes. The reaction mixture is stirred at room temperature for 2 hours. The reaction solution is cooled to 0° C. and was added with saturated Na$_2$SO$_3$ aqueous solution until the reaction color becomes colorless. The stirring is stopped and the organic layer iseparated and the aqueous layer is extracted with EtOAc (3 vol×3). The organic layers are combined and concentrated in vacuo until the total volume becomes 3 vol. The resulting solution was extracted with 1 N NaOH (3 vol× 3) and the remaining organic layer was discarded. The combined aqueous solution was acidified with 6 N HCl until the pH became 1.0. The solution is extracted with CH$_2$Cl$_2$ (3 vol×5). The combined organic layer are dried over MgSO$_4$ and concentrated to get the product (i.e., compound 4).

Step 4. Amidation
((E)-N-cyclopropylhex-2-enamide)

To a three-neck 250 mL round bottom flask equipped with mechanical stirrer and reflux condenser is charged 2-hexenoic acid-3d (10 g, 0.09 mole), IBCF (13 g, 1.1 eq) in CH$_2$Cl$_2$ (100 mL, 10 vol). The resulting solution is cooled to 0° C. and NMM (13.2 g, 1.5 eq) was added slowly by controlling the temperature between 0 and 20° C. Then, the mixture is allowed to warm to room temperature and stirred for 1 hour. To the resulting solution is added cyclopropyl amine (5.9 g, 1.2 eq) and the solution stirred for 2 hours. The reaction mixture is washed with 1 N NaOH (3 vol×2), 1 N HCl (3 vol×2), and brine solution (3 vol), and water (3 vol). The organic layer is dried over MgSO$_4$ and concentrated to afford the crude product as oil. The crude product is dissolved with heptane (5 vol) and cooled to −78° C. with stirring. The precipitated solid is filtered and dried to give the product (i.e., compound 5).

Step 5. Epoxidation
(N-cyclopropyl-3-propyloxirane-2-carboxamide)

To a three-neck 250 mL round bottom flask equipped with mechanical stirrer and containing (E)-N-cyclopropylhex-2-enamide-3d 5 (10 g, 0.06 mole), urea hydrogen peroxide (25 g, 4 eq), and p-TsOH (12.3 g, 1 eq) in CH$_2$Cl$_2$ (100 mL, 10 vol) at 0° C. is added trifluoroacetic anhydride (40.9 g, 3 eq) in CH$_2$Cl$_2$ (50 mL, 5 vol) over 30 minutes. The reaction mixture is heated to 40±5° C. and stirred for 3 hours. After cooling to 0° C., the reaction is quenched by adding 6 N NaOH (100 mL, 10 vol) slowly and stirring for 30 minutes. The organic layer is separated, washed with brine (5 vol) and water (5 vol). The resulting organic layer is dried over MgSO$_4$ and solvent evaporated to afford the epoxide product (i.e., compound 6), which is used for the next step without further purification.

Step 6. Azide Formation
(3-azido-N-cyclopropyl-2-hydroxyhexanamide)

To a three necked 250 mL round bottom flask equipped with mechanical stirrer and reflux condenser containing the epoxide-3d 6 (10 g, 0.06 mole) and anhydrous magnesium sulfate (14.1 g, 2.0 eq) in MeOH (100 mL, 10 vol) is added sodium azide (15.3 g, 4.0 eq) in one portion. The resulting mixture is heated to 65±5° C. and stirred for 5 hours. The reaction solution is cooled to the room temperature and IPAC (100 mL, 10 vol) is added and stirred for 10 minutes. The mixture is filtered through a pad of Celite® to remove insoluble salts and the resulting clear solution is concentrated to 3 vol. To the resulting solution is added IPAC (170 mL, 17 vol) and the mixture is stirred for 10 minutes. Again, the solution is filtered through a pad of Celite® to afford the product, the azide-3d (i.e., compound 7) as a solution in IPAC (about 200 mL) for the next step without further purification.

Step 7. Hydrogenation (Racemic warhead)

To a 500 mL of autoclave hydrogenation reactor equipped with mechanical stirrer containing the azide-3d (i.e., compound 7) (200 mL, 0.05 mole) in IPAC obtained in the previous step in a hydrogenation reactor is charged Pd/C (10% Pd, water 50%, 0.8 g). The solution is charged with nitrogen (1.0 atm) and released three times and then charged with hydrogen (3.0 atm) and released three times. The resulting solution is charged with hydrogen (3 atm) and stirred for 5 hours. After releasing the hydrogen gas, the solution is purged with nitrogen for 5 minutes. To the resulting solution was added MeOH (30 ml, 3 vol) and the reaction mixture is heated to 50±5° C. The reaction mixture is filtered through a pad of Celite® to afford a clear solution. The product is isolated by concentrating the solution at 20±5° C. until 3 vol of the solution remains. The solid is collected by filtration, washed (IPAC, 3 vol), and dried to give the product (i.e., compound 8).

Step 8. Resolution of
3-amino-N-cyclopropyl-2-hydroxyhexanamide

I. Salt Formation

To a three-neck 250 mL round bottom flask equipped with mechanical stirrer and containing the racemic 3-amino-N-cyclopropyl-2-hydroxyhexanamide (10 g, 0.05 mole) in THF (100 mL, 10 v) is charged deoxycholic acid (15.7 g, 0.75 eq.). The reaction mixture is heated to 65±5° C. and stirred for 1 hour at the temperature. The resulting homogeneous mixture was cool down to 23±2° C. over 1 hour, and it was maintained at the same temperature range for 1 hour. The precipitated solids were collected by filtration, washed with THF (50 mL, 5 vol), dried to give a salt.

To a three-neck 250 mL round bottom flask equipped with mechanical stirrer ischarged the salt (obtained in previous step) and 2-propanol (62 mL, 5 vol). The solution is heated to 75±5° C. and 5 to 6 N HCl solution in IPA (12 mL, 3 eq.) is added slowly with vigorous stirring. The resulting solution is stirred at the same temperature for 1 hour and cooled to 23±2° C. The reaction mixture is maintained at the same temperature for 1 hour. The precipitated solids are collected by filtration, washed with 2-propanol (36 mL, 3 vol), dried to give (2S,3S)-3-amino-N-cyclopropyl-2-hydroxyhexanamide hydrochloride (Enantiomeric Ratio=0:100).

Other Embodiments

It is to be understood that while the invention has been described in conjunction with the detailed description thereof, the foregoing description is intended to illustrate and not limit the scope of the invention, which is defined by the scope of the following claims. Other aspects, advantages, and modification are within the scope of the following claims.

What is claimed is:
1. A compound which is 3-amino-N-cyclopropyl-2-hydroxyhexanamide, deoxycholic acid salt.

* * * * *

UNITED STATES PATENT AND TRADEMARK OFFICE
CERTIFICATE OF CORRECTION

PATENT NO. : 8,383,858 B2  
APPLICATION NO. : 12/806014  
DATED : February 26, 2013  
INVENTOR(S) : Gerald J. Tanoury et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this  
Eighth Day of October, 2013

Teresa Stanek Rea  
*Deputy Director of the United States Patent and Trademark Office*